(12) United States Patent
Lentz

(10) Patent No.: US 6,955,673 B2
(45) Date of Patent: Oct. 18, 2005

(54) HEAT TRANSFER SEGMENT FOR A CRYOABLATION CATHETER

(75) Inventor: David J. Lentz, La Jolla, CA (US)

(73) Assignee: CryoCor, Inc., San Diego, CA (US)

( * ) Notice: Subject to any disclaimer, the term of this patent is extended or adjusted under 35 U.S.C. 154(b) by 40 days.

(21) Appl. No.: 10/222,770

(22) Filed: Aug. 16, 2002

(65) Prior Publication Data

US 2004/0034345 A1    Feb. 19, 2004

(51) Int. Cl.[7] .............................................. A61B 18/18
(52) U.S. Cl. ...................................................... 606/21
(58) Field of Search .................................... 606/20–26

(56) References Cited

U.S. PATENT DOCUMENTS

| | | |
|---|---|---|
| 3,696,813 A | 10/1972 | Wallach |
| 3,913,581 A | 10/1975 | Ritson et al. |
| 4,018,227 A | 4/1977 | Wallach |
| 5,139,496 A | 8/1992 | Hed |
| 5,281,213 A | 1/1994 | Milder et al. |
| 5,281,215 A | 1/1994 | Milder |
| 5,322,508 A | 6/1994 | Viera |
| 5,423,807 A | 6/1995 | Milder |
| 5,759,182 A | 6/1998 | Varney et al. |
| 5,833,685 A | 11/1998 | Tortal et al. |
| 5,876,399 A | 3/1999 | Chia et al. |
| 5,899,898 A | 5/1999 | Arless et al. |
| 5,899,899 A * | 5/1999 | Arless et al. .................. 606/22 |
| 5,992,158 A | 11/1999 | Goddard et al. |
| 6,024,740 A | 2/2000 | Lesh et al. |
| 6,048,919 A | 4/2000 | McCullough |
| 6,117,101 A | 9/2000 | Diederich et al. |
| 6,139,544 A | 10/2000 | Mikus et al. |
| 6,235,019 B1 | 5/2001 | Lehmann et al. |
| 6,251,105 B1 | 6/2001 | Mikus et al. |
| 6,280,439 B1 | 8/2001 | Martin et al. |
| 6,283,959 B1 * | 9/2001 | Lalonde et al. ................ 606/21 |
| 6,367,541 B2 | 4/2002 | McCullough |
| 6,383,180 B1 | 5/2002 | Lalonde et al. |
| 6,407,149 B1 | 6/2002 | McCullough |
| 6,464,716 B1 * | 10/2002 | Dobak et al. ................ 607/105 |
| 6,468,268 B1 | 10/2002 | Abboud et al. |
| 6,471,693 B1 | 10/2002 | Carroll et al. |
| 6,527,769 B2 | 3/2003 | Langberg et al. |
| 6,540,740 B2 | 4/2003 | Lehmann et al. |
| 6,562,030 B1 | 5/2003 | Abboud et al. |

(Continued)

FOREIGN PATENT DOCUMENTS

| | | |
|---|---|---|
| EP | 1 008 327 A2 | 6/2000 |
| GB | 2 236 253 A | 4/2001 |

*Primary Examiner*—Michael Peffley
(74) *Attorney, Agent, or Firm*—Nydegger & Associates

(57) ABSTRACT

A heat transfer segment for a cryoablation catheter includes a member, at least a portion of which is made of a thermally conductive composite material. The composite material includes a polymeric matrix material such as a polyether block amide (PEBA) and a filler material which can include metals, metal alloys, ceramics, carbon and combinations thereof. One particular composition for the composite material includes approximately twenty weight percent of filler material, with the balance being polymeric matrix material. The composite has a thermal conductivity that is significantly increased relative to the polymeric matrix material and a flexibility that is not significantly reduced relative to the polymeric matrix material. In use, the heat transfer segment is disposed within a patient's body and positioned adjacent target tissue. A refrigerant is then introduced into the heat transfer segment causing heat to flow from the target tissue, through the member and into the refrigerant.

13 Claims, 3 Drawing Sheets

U.S. PATENT DOCUMENTS

| | | |
|---|---|---|
| 6,569,158 B1 | 5/2003 | Abboud et al. |
| 6,575,933 B1 | 6/2003 | Wittenberger et al. |
| 6,575,966 B2 | 6/2003 | Lane et al. |
| 6,579,287 B2 | 6/2003 | Wittenberger et al. |
| 6,585,717 B1 | 7/2003 | Wittenberger et al. |
| 6,585,728 B2 | 7/2003 | Heiner et al. |
| 6,585,729 B1 | 7/2003 | Eum |
| 6,589,234 B2 | 7/2003 | Lalonde et al. |
| 6,592,577 B2 | 7/2003 | Abboud et al. |
| 6,595,988 B2 | 7/2003 | Wittenberger et al. |
| 6,602,247 B2 | 8/2003 | Lalonde |
| 6,602,276 B2 * | 8/2003 | Dobak et al. ............... 607/105 |
| 6,605,087 B2 | 8/2003 | Swartz et al. |
| 6,629,972 B2 | 10/2003 | Lehmann et al. |
| 6,635,053 B1 | 10/2003 | Lalonde et al. |
| 6,733,494 B2 | 5/2004 | Abboud et al. |
| 6,755,823 B2 | 6/2004 | Lalonde |
| 6,761,714 B2 | 7/2004 | Abboud et al. |
| 2001/0021847 A1 | 9/2001 | Abboud et al. |
| 2001/0025075 A1 | 9/2001 | Smith et al. |
| 2002/0025998 A1 | 2/2002 | McCullough et al. |
| 2002/0062122 A1 | 5/2002 | Lehmann et al. |
| 2002/0091378 A1 * | 7/2002 | Dobak et al. ............... 606/21 |
| 2002/0111612 A1 | 8/2002 | Lalonde et al. |
| 2002/0115989 A1 | 8/2002 | Abboud et al. |
| 2003/0004504 A1 | 1/2003 | Abboud et al. |
| 2003/0009160 A1 | 1/2003 | Carroll et al. |
| 2003/0018326 A1 | 1/2003 | Abboud et al. |
| 2003/0097124 A1 | 5/2003 | Lehmann et al. |
| 2004/0049178 A1 | 3/2004 | Abboud et al. |
| 2004/0054361 A1 | 3/2004 | Lehmann et al. |

* cited by examiner

US 6,955,673 B2

HEAT TRANSFER SEGMENT FOR A CRYOABLATION CATHETER

FIELD OF THE INVENTION

The present invention pertains generally to catheters. More particularly, the present invention pertains to catheters for cryoablating internal tissue. The present invention is particularly, but not exclusively, useful as a segment of a cardiac cryoablation catheter for transferring heat from target tissue to a refrigerant.

BACKGROUND OF THE INVENTION

Atrial fibrillation is an irregular heart rhythm that adversely affects approximately 2.5 million people in the U.S. It is believed that at least one-third of all atrial fibrillation originates near the ostium of the pulmonary veins, and that the optimal treatment technique is to ablate these focal areas through the creation of circumferential or linear lesions around the ostia of the pulmonary veins.

Heretofore, the standard ablation platform has been radio-frequency energy. However, radio-frequency energy technology is not amenable to safely producing circumferential lesions without the potential for some serious complications, including stenosis and stroke. In addition, the ablation of myocardial cells with heating energy also alters the extracellular matrix proteins, causing the matrix to collapse. Also, radio-frequency energy is known to damage the lining of the heart, which may account for thromboembolic complications.

Cryoablation of myocardial tissue has a long, successful history of use in open-heart surgery. Further, the use of cryoablation does not seem to cause extracellular matrix changes or do damage to the endocardium, allowing the correct lesion size to be created for therapeutic benefit. The cooling associated with cryoablation also has the natural tendency to freeze stationary tissue, rather than flowing blood. As a consequence, clot-related complications are greatly reduced.

Cryoablation of myocardial tissue via a catheter reduces many of the complications associated with open-heart surgery. Still, there are several complications that must be overcome to efficiently deliver cryo-energy to myocardial tissue. For example, a low temperature medium such as a refrigerant must be delivered to the general location of the tissue to be cryoablated. Thus, the catheter must contain structures for delivering the refrigerant to the target area and for transferring heat from the target tissue to the refrigerant. To reach the target area, these catheter structures must be advanced through portions of a patient's vasculature, often along extremely tortuous paths. Note; for purposes of this disclosure, the term "vasculature" including derivatives thereof, is herein intended to mean any cavity or lumen within the body which is defined at least in part by a tissue wall, to specifically include the cardiac chambers, arterial vessels and the venous vessels. Thus, the entire catheter must be considerably flexible and generally must contain some mechanism to steer the catheter as the catheter navigates through the vasculature.

Another factor that must be considered when contemplating the use of a catheter to cryoablate myocardial tissue for the treatment of atrial fibrillation is the electrical conductivity of the materials used to construct the catheter. Specifically, the cryoablation catheter may include an electrode to first map cardiac electrical signals for the purpose of selecting target tissue for cryoablation. In this case, it is generally desirable that the catheter be constructed of materials that are electrical insulators to avoid the interference with the mapping electrode. On the other hand, thermally conductive materials are generally required to transfer heat from the target tissue to the refrigerant.

In light of the above it is an object of the present invention to provide a catheter for cryoablating internal tissue. It is yet another object of the present invention to provide a segment for a cardiac cryoablation catheter for transferring heat from target tissue to a refrigerant. Yet another object of the present invention is to provide a heat transfer segment for a cryoablation catheter that is flexible enough to be advanced through the vasculature of a patient and positioned adjacent preselected myocardial tissue. It is still another object of the present invention to provide a heat transfer segment for a cryoablation catheter that also functions as an articulation segment that is controllable from an extracorporeal location to steer the catheter during advancement of the catheter through the vasculature of a patient. Still another object of the present invention is to provide a heat transfer segment for a cryoablation catheter that can be selectively deflected from an extracorporeal location to reconfigure the distal end of the catheter into a selected shape near the tissue to be cryoablated. It is yet another object of the present invention to provide a heat transfer segment for a cryoablation catheter having a selective distribution of thermally conductive material to allow for the cryoablation of selectively shaped lesions to include annular shaped lesions and linear shaped lesions. Still another object of the present invention is to provide a heat transfer segment for a cryoablation catheter that does not interfere with the catheter's mapping electrode. Yet another object of the present invention is to provide a catheter and a method of use for cryoablation of tissue which is easy to use, relatively simple to manufacture, and comparatively cost effective.

SUMMARY OF THE INVENTION

The present invention is directed to a heat transfer segment for a cryoablation catheter. In use, the heat transfer segment is disposed within a patient's body and positioned adjacent target tissue. A refrigerant is then introduced into the heat transfer segment causing heat to flow from the target tissue, through the heat transfer segment and into the refrigerant.

In greater structural detail, the heat transfer segment includes a member, at least a portion of which is made of a composite material that is thermally conductive. More specifically, the composite material includes a polymeric matrix material and a filler material. A preferred polymeric matrix material is a polyether block amide (PEBA) such as PEBAX®. As will be appreciated by the skilled artisan, several thermoplastic polyurethanes and elastomeric polyesters may be used. A preferred composition for the composite material includes between approximately ten weight percent and thirty weight percent (10 wt. %–30 wt. %) of filler material, with the balance being polymeric matrix material. In some instances it may be desirable to use higher percentages of filler material (e.g. 50 wt. %–80 wt. %), so long as the matrix is not overwhelmed. A more preferred composition for the composite material includes approximately twenty weight percent (20 wt. %) of filler material, with the balance being polymeric matrix material. At this composition, the thermal conductivity is significantly increased relative to the polymeric matrix material while the flexibility (i.e. flexural modulus or modulus of elasticity) of the composite material is not significantly reduced relative to the polymeric matrix material.

Suitable filler materials for use in the present invention include, but are not limited to metals, metal alloys, ceramics, carbon and combinations thereof. Furthermore, within the composite material, the filler material(s) can vary in terms of particle size, shape, orientation and distribution. Suitable shapes for use in the present invention include, but are not limited to flakes, elongated shapes to include needles and fibers, and powders to include spheroidally shaped particles. The composite material can be formulated to have an electrical conductivity that is significantly increased relative to the polymeric matrix material, for example, by using carbon in the filler material. On the other hand, for applications wherein a significantly increased electrical conductivity is undesirable, a suitable composite material can be formulated, for example, by using a ceramic in the filler material. One such application is where the catheter includes an electrode to first map cardiac electrical signals for the purpose of selecting target tissue for cryoablation. In this case, it is generally desirable that the catheter be constructed of materials that are electrical insulators to avoid the interference with the mapping electrode.

In a particular embodiment of the present invention, the member is shaped as an elongated tube having a lumen. At least one portion of the tube is made of the composite material while the remaining portion of the tube is made of the polymeric matrix material. For the present invention, the entire tube can be made of the composite material or only a portion. Typical portion shapes can include, but are not limited to an annular portion of the tube, an elongated portion of the tube that extends substantially parallel to the direction of tube elongation and a spot shape at a pre-selected location on the tube. It is to be appreciated that the shape and location of the composite portion will determine the amount and location of tissue that will be cryoablated when a refrigerant is disposed within the lumen of the tube.

In another particular embodiment of the present invention, the heat transfer segment includes the elongated tube as described above, and a mechanism to control bending of the elongated tube from an extracorporeal location while the member is positioned within a patient's body. Thus, the heat transfer segment can also function as an articulation segment. For this purpose, it is to be appreciated that the tube will be flexible. As indicated above, the amount of filler material that is added to the polymeric matrix material can be controlled to ensure that the composite material is flexible. With this cooperation of structure, the mechanism can be used to selectively reconfigure the shape of the tube to steer the heat transfer segment and catheter through the vasculature of the body, to conform the tube to a desired shape near the target tissue, or both. One mechanism that can be used to controllably bend the elongated tube includes a control wire that is attached to the heat transfer segment near the distal end of the segment. From the distal end of the segment, the control wire extends to an extracorporeal location, where the control wire can be manipulated. The heat transfer segment can also include a flexible spine, made of a material having a greater flexural modulus than the elongated tube, to cooperate with the control wire to ensure that the tube bends in a pre-selected bend plane in response to a movement of the control wire. If desired, the spine can be made with composite materials rendering it thermally or electrically conductive.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENT

Figure 1:
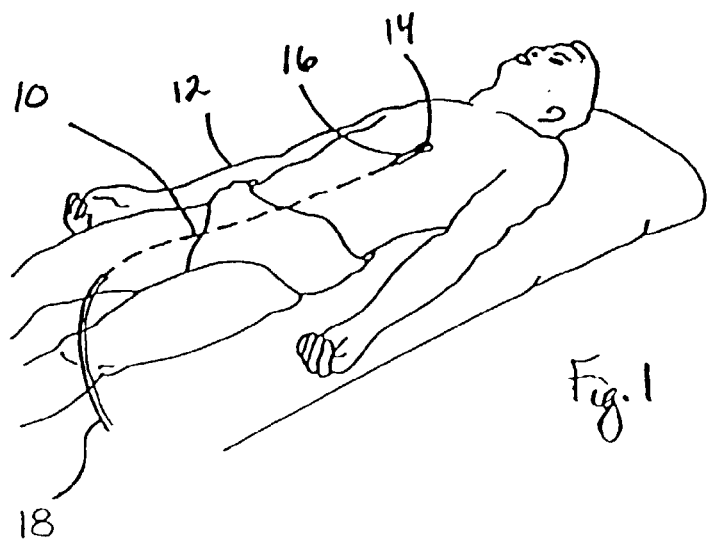
FIG. 1 is a perspective view of a catheter incorporating the heat treatment segment of the present invention, as it is being advanced into the vasculature of a patient for an invasive procedure.

Referring initially to FIG. 1, a catheter for cryoablating internal target tissue in accordance with the present invention is shown and is designated 10. In FIG. 1, the catheter 10 is shown as it is being positioned in the vasculature of a patient 12. As further shown, the catheter 10 includes a distal tip 14 that is located at the distal end of the catheter 10 and a heat transfer segment 16 that is attached proximal to the distal tip 14. Still further, a catheter tube 18 is attached proximal to the heat transfer segment 16. In use, the catheter 10 is advanced until the heat transfer segment 16 is positioned adjacent the target tissue. Once the catheter 10 is positioned, a low temperature refrigerant is then introduced into the heat transfer segment 16, causing heat to flow from the target tissue, through the heat transfer segment 16 and into the refrigerant. This results in the cryoablation of the target tissue.

Figure 2:
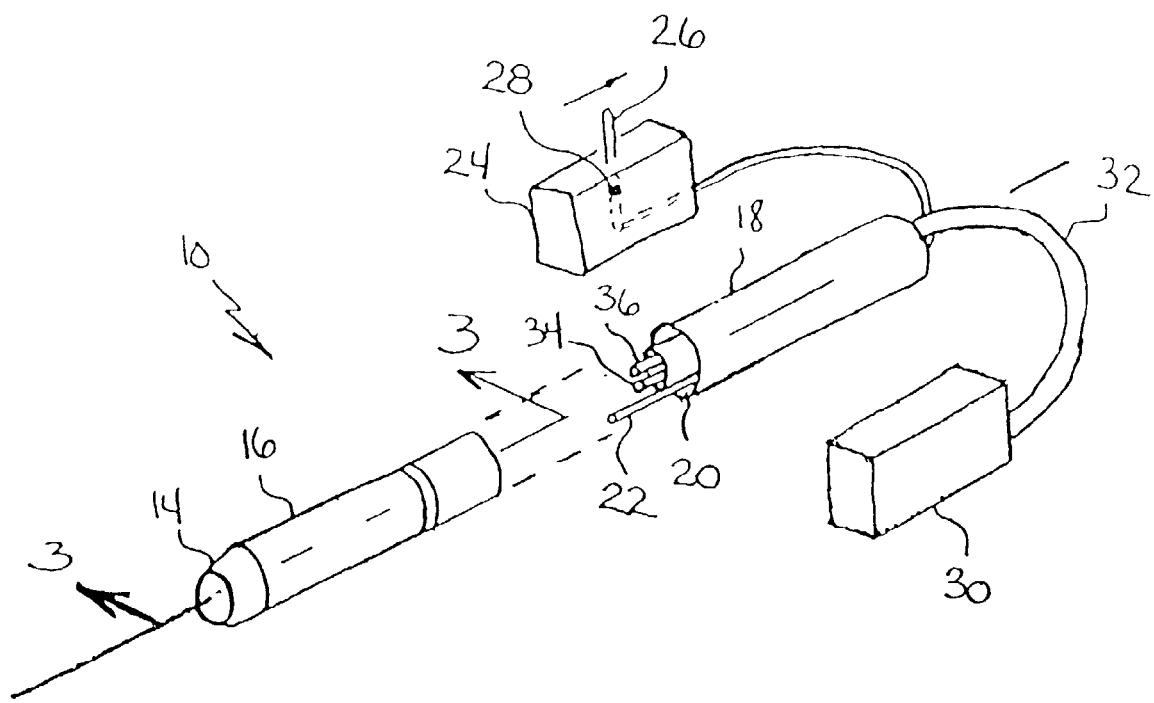
FIG. 2 is a segmented, perspective view of a cryoablation catheter having the heat treatment segment of the present invention.
Figure 3:
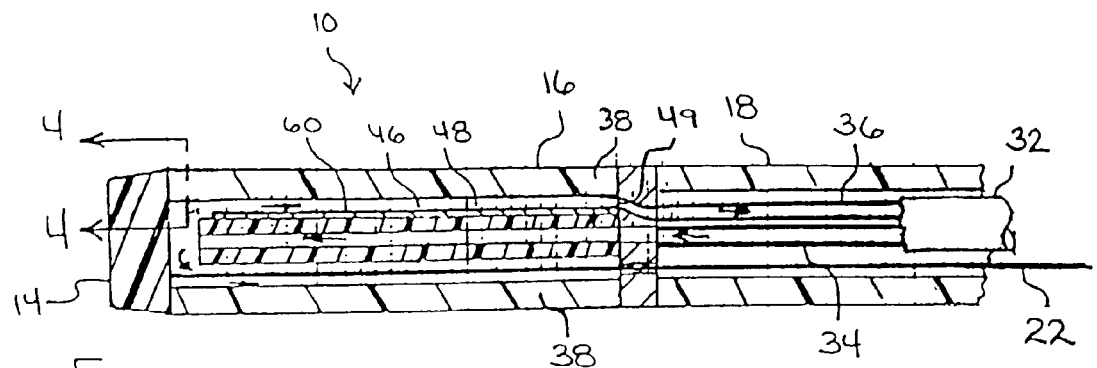
FIG. 3 is a sectional view of the distal end portion of the catheter shown in FIG. 2 as seen along the line 3—3 in FIG. 2.

Referring now to FIG. 2, it will be seen that the catheter tube 18 is formed with a lumen 20 that extends the length of the catheter tube 18. Further, FIG. 2 indicates that a deflection control wire 22 extends through the lumen 20 from an extracorporeal control mechanism 24. In particular, the control mechanism 24 includes a pivot arm 26 which can be rotated about the pivot point 28 by an operator (not shown) to exert a proximally directed force on the deflection control wire 22. It will be appreciated by the skilled artisan that the control mechanism 24 shown in FIG. 2 is only exemplary and that any device known in the pertinent art for generating an axial force on the deflection control wire 22 is suitable for the present invention. As best seen in FIG. 3, the deflection control wire 22 extends through the heat transfer segment 16 and attaches to the distal tip 14.

Referring back to FIG. 2, the catheter 10 is shown to include a refrigerant source 30, which is to be used for the purpose of supplying a fluid that can be cooled to approximately minus eighty degrees Celsius. In a particular embodiment of the present invention, a medical gas, such as nitrous oxide, is used as the refrigerant. With cross reference to FIGS. 2 and 3 it can be seen that the catheter 10 includes a tube 32 that extends from the refrigerant source 30 and through the lumen 20 of the catheter tube 18 to the heat transfer segment 16. As further shown, tube 32 includes a feed line 34 to deliver refrigerant from the refrigerant source 30 to the heat transfer segment 16 and a return line 36 to deliver refrigerant back to the refrigerant source 30 from the heat transfer segment 16.

Figure 4:
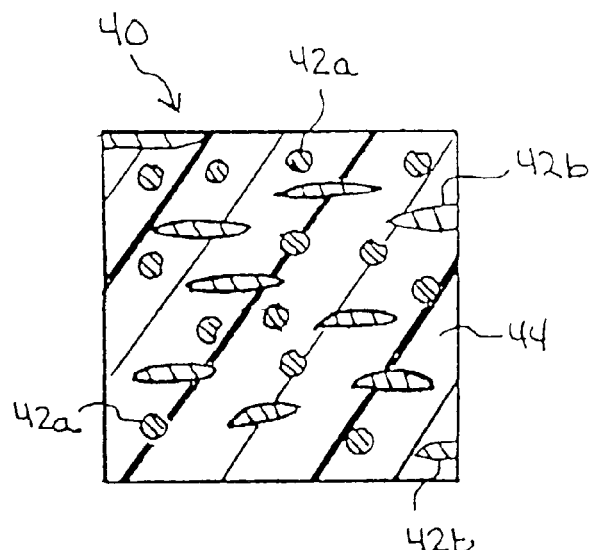
FIG. 4 is a sectional view of the heat treatment segment member that is made of an exemplary thermally conductive composite material as would be seen along line 4—4 in FIG. 3.

Referring now to FIG. 3, it can be seen that the heat transfer segment 16 includes a member 38. Importantly for the present invention, as best seen in FIG. 4, the member 38 is made of a composite material 40 that is thermally conductive. As detailed further below, the entire member 38 can be made of the composite material 40 (as shown for the exemplary member 38 in FIG. 3) or one or more portions of the member 38 can be made of a composite material 40. In accordance with the present invention, the member 38 can be manufactured using plastic fabrication processes such as extrusion and injection molding to include co-injection. As shown in FIG. 4, the composite material includes a filler material 42 (shown as exemplary filler material 42a and exemplary filler material 42b in FIG. 4) embedded in a polymeric matrix material 44. A preferred polymeric matrix material 44 is a polyether block amide (PEBA) such as PEBAX®. Typical properties for the polymeric matrix material 44 include a flexural modulus in the range of 20–455 MPa and thermal conductivity in the range of 0.2–0.3 W/m° K. By itself, the polymeric matrix material 44 is considered to be flexible and is considered to be both an electrical and thermal insulator.

A preferred composition for the composite material 40 includes between approximately ten weight percent and thirty weight percent (10 wt. %–30 wt. %) of filler material 42 with the balance being polymeric matrix material 44. A more preferred composition for the composite material 40 includes approximately twenty weight percent (20 wt. %) of filler material 42, with the balance being polymeric matrix material 44. For a composite 40 having this more preferred composition, the thermal conductivity is significantly increased relative to the polymeric matrix material 44 while the flexibility (i.e. flexural modulus or modulus of elasticity) of the composite material 40 is not significantly reduced relative to the polymeric matrix material 44. Typically, the composite material has a thermal conductivity greater than 1 W/m° K.

Suitable filler materials 42 for use in the present invention include, but are not limited to metals, metal alloys, ceramics, carbon and combinations thereof. Furthermore, within the composite material 40, the filler material 42 can vary in terms of particle size, shape, distribution and orientation (i.e. the filler material can be aligned in preselected direction(s) or randomly oriented. Suitable shapes for the filler material 42 include, but are not limited to flakes, elongated shapes to include needles and fibers, and powders to include spheroidally shaped particles. As shown in FIG. 4, the composite 40 can be formulated having more than one shape of filler material 42, such as spheroidally shaped filler material 42a in combination with elongated filler material 42b.

If desired, the composite material 40 can be formulated to have an electrical conductivity that is significantly increased relative to the polymeric matrix material 44, for example by using filler material 42 that includes carbon. On the other hand, for applications wherein a significantly increased electrical conductivity is undesirable, a suitable composite material 40 can be formulated, for example by using a filler material 42 that includes ceramics. One such application is where the catheter 10 includes an electrode (not shown) to first map cardiac electrical signals for the purpose of selecting target tissue for cryoablation. In this case, it is generally desirable that the catheter 10 be constructed of materials that are electrical insulators to avoid the interference with the mapping electrode.

Figure 5:
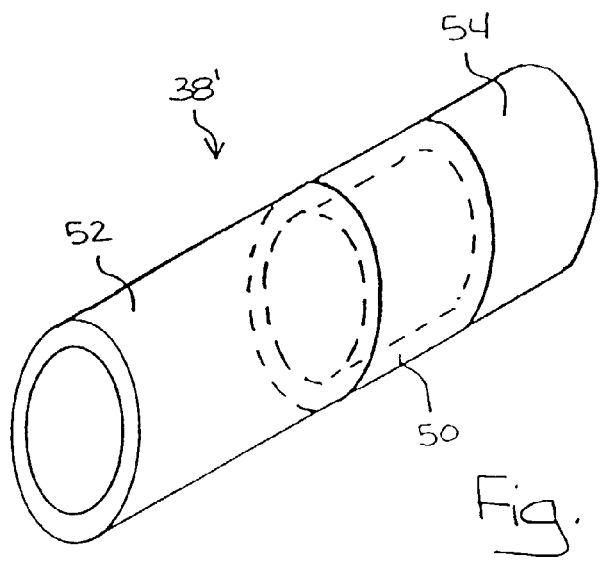
FIG. 5 is a perspective view of a particular embodiment of a heat treatment segment member of the present invention in which an annular portion of the member is made of a thermally conductive composite material and the remainder of the member is made of a polymeric matrix material.

In the particular embodiment of the present invention shown in FIGS. 2 and 3, the member 38 is shaped as an elongated tube. More specifically, the exemplary member 38 shown in FIGS. 2 and 3 is shaped as a hollow cylinder having a lumen 46. As further shown in FIG. 3, the lumen 46 includes a volume 48 in which a refrigerant can be disposed. An aperture 49 allows the volume 48 to receive refrigerant. As indicated above, the entire member 38 can be made of the composite material 40 (as shown for the exemplary member 38 in FIG. 3). Alternatively, as shown in FIG. 5, a member 38' can be formed having a portion 50 made of the composite material 40 (shown in FIG. 4) while the remaining portions 52, 54 are made of the same material as the polymeric matrix material (e.g. PEBA). As further shown in FIG. 5, the portion 50 can be shaped as an annulus. With this cooperation of structure (i.e. a thermally conductive annulus portion 50 disposed between two insulating portions 52, 54), the member 38' can be used to cryoablate a circumferentially shaped lesion.

Figure 6:
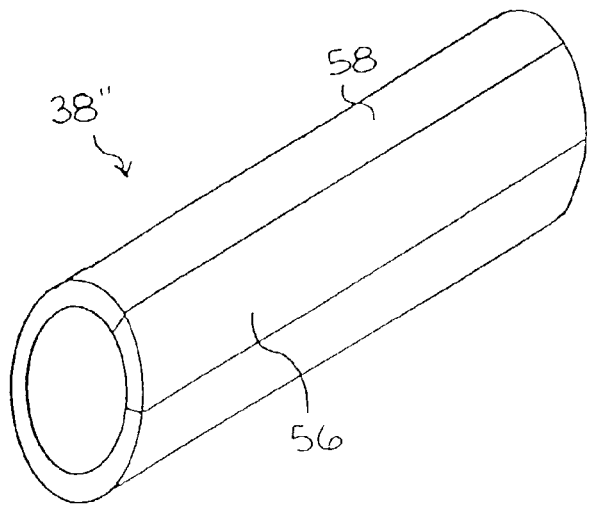
FIG. 6 is a perspective view of another particular embodiment of a heat treatment segment member of the present invention in which an elongated portion of the member is made of a thermally conductive composite material and the remainder of the member is made of a polymeric matrix material.

In another embodiment of the present invention, as shown in FIG. 6, a member 38" can be formed having an elongated portion 56 made of the composite material 40 (shown in FIG. 4) while the remaining portion 58 is made of the same material as the polymeric matrix material (e.g. PEBA). As further shown in FIG. 6, the elongated portion 56 can extend substantially parallel to the direction of tube elongation. With this cooperation of structure (i.e. a tubular shaped member 38" having a thermally conductive elongated portion 56), the member 38" can be used to cryoablate a linear shaped lesion.

Figure 7:
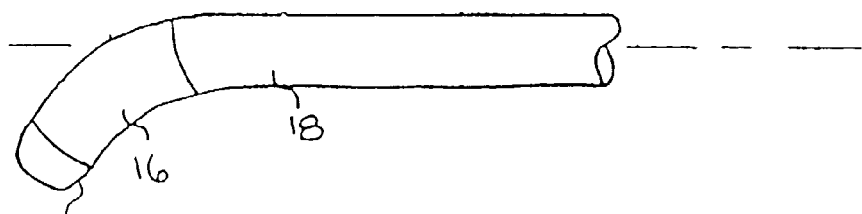
FIG. 7 is a perspective view of the distal end portion of the catheter shown in FIG. 2, shown after deflection of the distal tip.

With cross-reference now to FIGS. 3 and 7, it can be seen that the heat transfer segment 16 shown in FIG. 3 can also function as an articulation segment. As indicated above, the concentration of filler material 42 in the composite material 40 can be controlled to ensure that the member 38 is flexible enough to allow the heat transfer segment 16 to be deflected as shown in FIG. 7. With the heat transfer segment 16 positioned within a patient's body, the control mechanism 24 can be selectively activated from an extracorporeal location to controllably bend the heat transfer segment 16. As shown in FIG. 3, the heat transfer segment 16 can also include a flexible spine 60, made of a material having a greater flexural modulus than the member 38, to cooperate with the deflection control wire 22 to ensure that the heat transfer segment 16 bends in a pre-selected bend plane in response to a movement of the deflection control wire 22. Selectively reconfiguring the shape of the heat transfer segment 16 in this manner can be performed to steer the catheter 10 through the vasculature of the body or to obtain a pre-selected shape for heat transfer segment 16 at the target tissue.

While the particular Heat Transfer Segment For A Cryoablation Catheter as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A heat transfer segment for a cryoablation catheter, said heat transfer segment comprising:

a non-inflatable tubular member shaped to enclose a volume and having an aperture for receiving a refrigerant therein with at least one portion of said member being made of a composite material having an elongated shape, said remaining portion being made of a polymeric matrix material, wherein said composite material has a first flexular modulus and said polymeric matrix material has a second flexular modulus, said composite material including filler material particles embedded in a polymeric matrix material, with said composite material having a thermal conductivity greater than said polymeric matrix material to transfer heat from tissue to the refrigerant during cryoablation; and a means for controllably bending said member from an extracorporeal location while said member is positioned within a patient's body wherein a difference between the first flexural modulus and the second flexural modulus biases said member to bend in a pre-selected bend plane, to steer said catheter through the body and position the composite material portion adjacent the target tissue.

2. A heat transfer segment as recited in claim 1 wherein said polymeric matrix material is a polyether block amide.

3. A heat transfer segment as recited in claim 1 wherein said composite material includes between ten weight percent and thirty weight percent (10 wt. % –30 wt. %) of said filler material.

4. A heat transfer segment as recited in claim 1 wherein said filler material is selected from the group of fillers consisting of a metal, a metal alloy, a ceramic and carbon.

5. A catheter for cryoablating tissue, said catheter comprising:

a catheter tube;

a non-inflatable tubular member attached to said catheter tube, said member shaped to enclose a volume and having an aperture for receiving a refrigerant therein with at least one portion of said member being made of a composite material having an elongated shape, said remaining portion being made of a polymeric matrix material, wherein said composite material has a first flexular modulus and said polymeric matrix material has a second flexular modulus, said composite material including filler material particles embedded in a polymeric matrix material, with said composite material having a thermal conductivity greater than said polymeric matrix material;

a means for controllably bending said member from an extracorporeal location while said member is positioned within a patient's body wherein a difference between the first flexural modulus and the second flexural modulus biases said member to bend in a pre-selected bend plane, to steer said catheter through the body and position the composite material portion adjacent the target tissue; and a means for introducing a refrigerant into said volume to draw heat from said tissue and through said portion of said member.

6. A catheter as recited in claim 5 wherein said polymeric matrix material is a polyether block amide.

7. A catheter as recited in claim 5 wherein said composite material includes between ten weight percent and thirty weight percent (10 wt. %–30 wt. %) of said filler material.

8. A catheter as recited in claim 5 wherein said filler material is selected from the group of fillers consisting of a metal, a metal alloy, a ceramic and carbon.

9. A catheter as recited in claim 5 wherein said composite material has a thermal conductivity greater than 1 W/m°K.

10. A method for cryoablating internal target tissue, said method comprising the steps of:

providing a catheter including a non-inflatable tubular member shaped to at least partially enclose a volume, with at least one portion of said member being made of a composite material having an elongated shape, said remaining portion being made of a polymeric matrix material, wherein said composite material has a first flexural modulus and said polymeric matrix material has a second flexural modulus, said composite material including filler material particles embedded in a polymeric matrix material, with said composite material having a thermal conductivity greater than said polymeric matrix material;

disposing said member into a body;

bending said member from an extracorporeal location to advance said catheter through the body to position said portion of said member being made of said composite material adjacent said target tissue, said member being biased to bend in a pre-selected bend plane by a difference between the first flexural modulus and the second flexural modulus; and introducing a refrigerant into said volume to cryoablate said target tissue.

11. A method as recited in claim 10 wherein said polymeric matrix material is a polyether block amide.

12. A method as recited in claim 10 wherein said composite material includes between ten weight percent and thirty weight percent (10 wt. %–30 wt. %) of said filler material.

13. A method as recited in claim 10 wherein said filler material is selected from the group of fillers consisting of a metal, a metal alloy, a ceramic and carbon.

* * * * *